United States Patent [19]

Hoppough

[11] Patent Number: 4,886,055

[45] Date of Patent: Dec. 12, 1989

[54] NEBULIZER DEVICE

[76] Inventor: John M. Hoppough, 921 S. Macomber, Greenville, Mich. 48838

[21] Appl. No.: 147,231

[22] Filed: Jan. 22, 1988

[51] Int. Cl.⁴ .............................................. A61M 11/02
[52] U.S. Cl. ........................... 128/200.14; 128/200.21; 128/203.12; 128/203.25
[58] Field of Search ................. 239/338; 128/200.14, 128/200.19, 200.21, 203.12, 203.16, 203.25, 203.29, 205.11, 200.18

[56] References Cited

U.S. PATENT DOCUMENTS

| Re. 30,046 | 7/1979 | van Amerongen | 239/338 |
|---|---|---|---|
| 733,027 | 7/1903 | Goldan | 128/203.25 |
| 1,176,886 | 3/1916 | Ermold | 128/203.25 |
| 3,547,351 | 12/1970 | Hruby, Jr. | 239/338 |
| 3,836,079 | 9/1974 | Huston | 239/338 |
| 3,913,607 | 10/1975 | Price | 128/205.11 |
| 04,243,396 | 1/1981 | Cronenberg | 239/338 |
| 4,267,974 | 5/1981 | Kienholz et al. | 128/203.25 |
| 4,319,566 | 3/1982 | Hayward et al. | 128/203.25 |
| 4,427,004 | 1/1984 | Miller | 128/200.21 |
| 4,595,002 | 6/1986 | Michaels et al. | 128/205.11 |
| 4,612,926 | 9/1986 | Boiarski et al. | 128/205.11 |
| 4,767,576 | 8/1988 | Bagwell | 128/200.21 |

FOREIGN PATENT DOCUMENTS

| 6911 | 3/1909 | United Kingdom | 128/205.11 |
|---|---|---|---|
| 616089 | 1/1949 | United Kingdom | 239/338 |

OTHER PUBLICATIONS

Armour Pharmaceutical Company Brochure, ARM-A-VIAL LV Large Volume Respiratory Therapy System.
Dec. 1987 issues, Respiratory Care, p. 1163.

Primary Examiner—William Pieprz
Assistant Examiner—Kimberly L. Asher
Attorney, Agent, or Firm—Price, Heneveld, Cooper, DeWitt & Litton

[57] ABSTRACT

A nebulizer device having an atmosphere adjusting collar both slidably and rotatably mounted on the housing so as to adjust restriction of atmosphere inlet ports on the housing. An additional high oxygen port on the nebulizing nozzle is restricted by a flow rate adjusting collar. The flow rate adjusting collar is coupled to the atmosphere adjusting collar so as to maintain rate of flow as the atmospheric inlet is adjusted, but the atmospheric inlet is automatically adjusted as the oxygen flow rate is adjusted. An atmosphere entraining valve located downstream of the nebulizer housing provides additional entrainment of atmosphere to further reduce the fraction of inspired oxygen in the humidified air.

33 Claims, 2 Drawing Sheets

NEBULIZER DEVICE

BACKGROUND OF THE INVENTION

The present invention relates to nebulizer devices, and in particular to nebulizer devices used in medical applications.

Nebulizers are used in medical environments to humidify the air supplied to a patient. Heretofore a wide variety of nebulizer designs have been developed and have been used with a variety of patient ventilating systems. In a typical system a nebulizer is coupled to a flowmeter which is in turn coupled to an oxygen source, such as an oxygen tank or hospital oxygen supply system. The flowmeter is used to adjust the oxygen flow rate supplied to the nebulizer. The nebulizer normally includes some type of nozzle that provides an air jet adjacent a fluid supply, which typically consists of a capillary tube that leads to a fluid supply bottle. The oxygen jet induces liquid flow up the capillary tube to the jet where the fluid is entrained as a fine aerosol mist. The humidified oxygen is then passed through tubing to some type of respiratory device, such as a respirator mask, endotracheal tube, oxygen tent or the like.

In the past nebulizers have also been used to regulate the oxygen concentration of the gas supplied to the patient, referred to as the "fraction of inspired oxygen" ($FIO_2$). For this purpose nebulizers typically have some type of valving system that allows atmospheric gas to vent into the oxygen flow at the nozzle region. The oxygen jet is used to entrain and mix with the atmospheric gases. Adjustment of the valving mechanism therefore regulates the atmosphere to oxygen ratio that is forced through the nebulizer device to the patient. However, since the oxygen flow through the nebulizer is used to induce a vacuum that draws atmosphere into the nozzle region as well as draws fluid up the capillary tube and into the oxygen stream, the size of the vent mechanism opening is limited. If an excessive atmospheric opening is provided, the fluid entraining oxygen will simply exhaust out through the vent mechanism rather than being directed toward the patient.

One substantial problem associated with previous nebulizers is the restriction of air flow to the patient. In instances in which the patient requires a low fraction of inspired oxygen, a relatively large amount of atmospheric gases may be drawn in through the nebulizer and supplied to the patient. In such an application the venting mechanism is fully opened, resulting in a high flow rate to the patient and a low fraction of inspired oxygen or oxygen percentage. In other instances, however, the patient may require a high fraction of inspired oxygen. In these applications the vent mechanism must be substantially closed, reducing the amount of atmospheric gases which are supplied to the patient and thus dramatically reducing the overall gas flow to the patient. Nonetheless the patient normally still requires a relatively high overall flow rate for respiration. In such instances one solution is to provide two nebulizer systems in order to double the flow rate to the patient yet maintain the appropriate fraction of inspired oxygen. Alternatively, the respiratory tubing downstream of the nebulizer may have an additional oxygen tube leading from another flowmeter which bleeds in oxygen to the previously humidified gas mixture. Although this permits the fraction of inspired oxygen to be increased, the atmosphere venting mechanism must be adjusted to accommodate this increased oxygen content and the nebulizer is not calibrated for this supplemented flow rate, so that this varying of the flow rate renders inaccurate the regulation of fraction of inspired oxygen. Inconsistent oxygen and flow delivered to the patient may result.

In another attempt to solve these problems, an additional valve has been placed on the nebulizer nozzle, which when opened permits additional oxygen to pass through another port on the nebulizer nozzle. This structure suffered from a similar problem as the flowmeter-nebulizer sequence noted above, in that the atmosphere venting mechanism is calibrated and accurate only as to a given flow rate of oxygen through the nebulizer. Changing this flow rate renders inaccurate the atmosphere venting mechanism and is a potential hazard.

In the above systems, inaccurate oxygen concentrations as a result of varying the flow rate can be potentially dangerous to the patient. The common practice of connecting a flowmeter and nebulizer poses such a potential hazard. Even in situations that do not pose a potential hazard to the patient, such multiple adjustments are confusing and difficult to estimate. Multiple systems require duplication of equipment which increases the expense of administering this type of therapy.

SUMMARY OF THE INVENTION

The present invention is preferably embodied in a nebulizer that provides adjustment both of the oxygen flow rate through the nebulizer and atmospheric flow into the nebulizer unit. The mechanism for adjusting the atmospheric inlet is coupled with the mechanism for adjusting the flow rate, so that as the flow rate is varied the atmospheric inlet is simultaneously adjusted. Nonetheless, adjustment of the atmospheric inlet does not necessarily adjust the flow rate through the nebulizer. This provides the nebulizer with the ability to increase the oxygen flow through the device in instances when very little atmospheric gases are to be mixed with the oxygen, yet maintain a properly calibrated atmospheric inlet and thus an appropriate fraction of inspired oxygen that is supplied through the unit. Further, for applications in which a very low fraction of inspired oxygen is desired, the nebulizer device provides an atmospheric inlet and atmosphere entraining nozzle located in the respiratory ducting between the nebulizer and the patient.

In a preferred embodiment the nebulizer provides a collar with atmospheric inlet apertures or vents slidably and rotatably mounted on the housing. A collar on the nebulizer nozzle opens an additional port or jet to increase oxygen flow. The two collars are coupled, while one atmosphere inlet is calibrated for single nozzle port flow and the other atmosphere inlet is calibrated for double nozzle port flow.

With the present nebulizer device a high flow rate is maintained even though a high fraction of inspired oxygen is provided through a single nebulizer device. The nebulizer device is quickly and easily adjusted, and additional flowmeters and the like are not required. The nebulizer device in a preferred embodiment provides a fraction of inspired oxygen range of from one hundred percent (1.0) to twenty eight percent (0.28). With an additional air entraining valve in the respiratory tube leading to the patient, the fraction of inspired oxygen is further reduced to a range of between twenty eight percent (0.28) and twenty four percent (0.24).

DETAILED DESCRIPTION OF THE PREFERRED EMBODIMENTS

Figure 1:
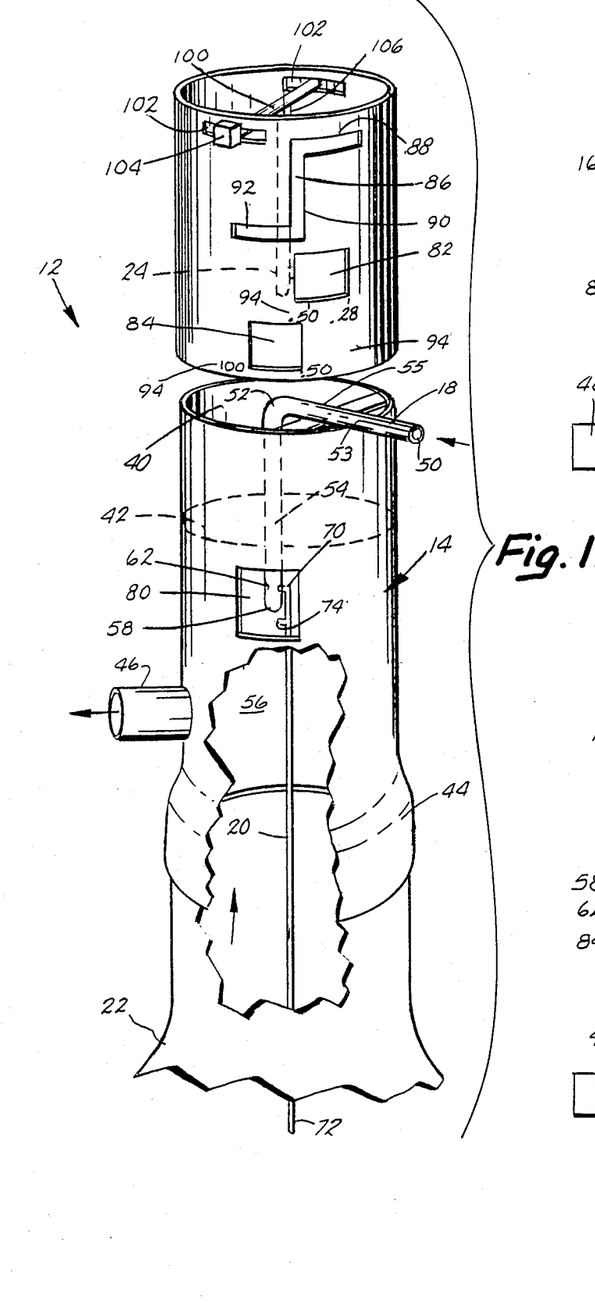
FIG. 1 is a fragmentary, exploded perspective view of a nebulizer device incorporating the present invention.
Figures 4, 5, 6, 10, 11:
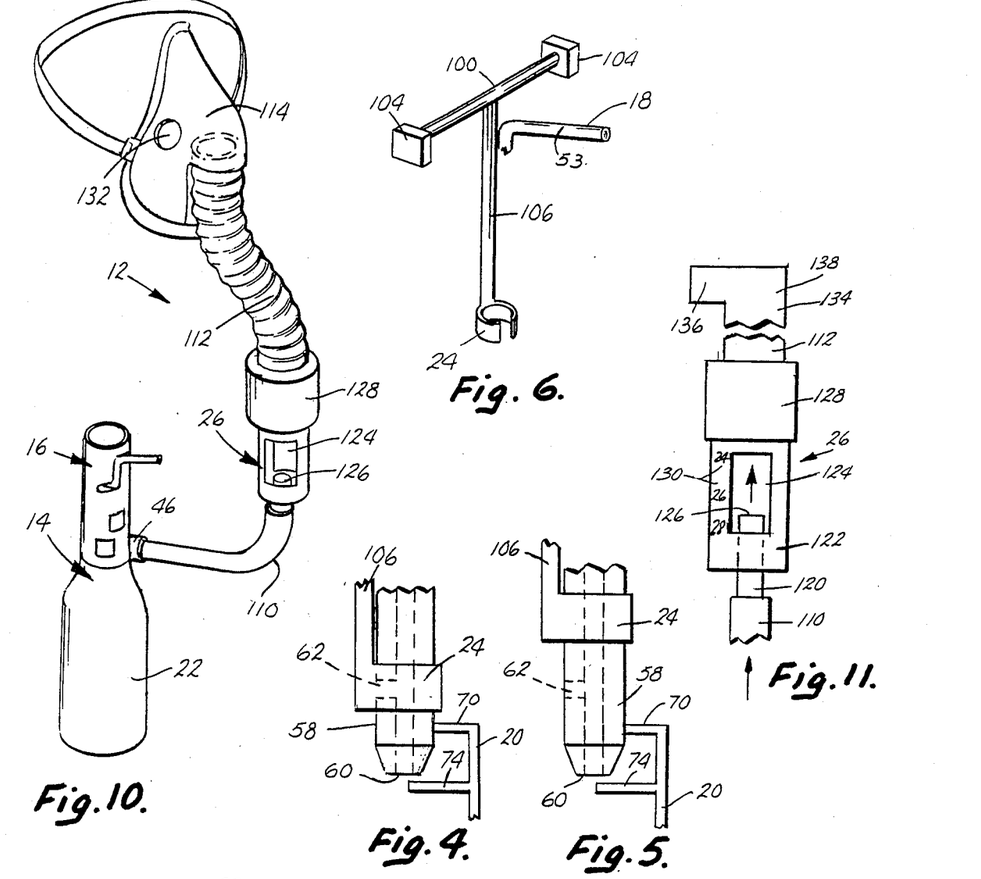
FIG. 4 is a fragmentary, front elevational view of the fluid entrainment or misting apparatus of the nebulizer device of FIG. 1, shown in a reduced flow rate condition.
FIG. 5 is a fragmentary, front elevational view of the fluid entrainment or misting apparatus of FIG. 4, shown in an increased flow rate condition.
FIG. 6 is a fragmentary, perspective view of an oxygen flow regulating valve used in the apparatus of FIGS. 4 and 5.
FIG. 10 is a perspective view of the nebulizer device of FIG. 1, shown connected to a respiratory mask and having an additional atmosphere entraining valve.
FIG. 11 is a fragmentary, elevational view of the additional atmosphere and entraining valve of FIG. 10.

The present invention is embodied in a nebulizer device, a preferred form of which is shown in FIGS. 1 and 10 and referenced generally by the numeral 12. Nebulizer device 12 includes a housing 14 on which a housing collar 16 is slidably mounted to regulate the flow of atmosphere into housing 14. An oxygen duct 18 extends down into housing 14. Duct 18 exhausts an oxygen jet past the upper opening of a capillary tube 20, which jet induces the drawing of fluid up through capillary tube 20 from a fluid reservoir 22. The fluid is thus entrained in the oxygen supplied to the patient. Housing collar 16 is coupled to a duct collar 24 which adjusts the oxygen flow through duct 18. With housing collar 16 coupled to duct collar 24, collar 16 is used to adjust the introduction of atmospheric gas through a predetermined range while a preselected oxygen flow rate is maintained. Collar 16 is also used to adjust duct collar 24 and thereby change the oxygen flow rate through housing 14 while simultaneously regulating the introduction of atmospheric gases in cooperation with this oxygen flow adjustment. An atmosphere entraining valve 26 (FIG. 10) located downstream of oxygen duct 18 and capillary tube 20 regulates the additional introduction of atmosphere to selectively further reduce the fraction of inspired oxygen yet maintain a moisturized gas flow to the patient.

As shown in FIG. 10. housing 14 has a generally cylindrical hollow tubular body with an open upper end 40. A top wall 42 closes off the upper end of housing 14 as well as provides a duct mounting support surface through which oxygen duct 18 passes. The open lower end of housing 14 is flared and threaded as a female coupling 44. Coupling 44 permits housing 14 to be threaded onto the top of fluid reservoir 22. A tubing outlet 46 extends from a lower sidewall region of housing 14. Tubing outlet 46 has a standard diameter for coupling to conventional respiratory tubing and provides an outlet passage through which the aerosol gases are supplied to the patient.

Oxygen duct 18 is a narrow L-shaped tube that is connected to an oxygen source via a coupling end 50. Preferably coupling end 50 is provided with a conventional diameter index safety system coupling so as to mate only with an oxygen supply nozzle. Coupling end 50 may therefore be connected directly to a conventional medical facility oxygen supply without requiring a flowmeter or other device to be first mounted on the oxygen wall outlet. Duct 18 includes a ninety degree elbow 52 that causes duct 18 to bend from a lateral arm 53 into a depending arm 54 that extends along the central axis of housing 14. Depending arm 54 passes through top wall 42 and projects down into a mixing chamber 56 formed by housing 14 beneath top wall 42. It is within mixing chamber 56 that liquid and atmospheric gases are entrained in the oxygen flow. An alternative mounting bracket 55 on housing upper end 40 is secured to lateral arm 53 to provide additional support to oxygen duct 18.

Depending arm 54 terminates in a nozzle 58 that supplies oxygen flow to mixing chamber 56. As best shown in FIGS. 4 and 5, a main oxygen end port 60 opens through the bottom or mixing end of duct 18. An additional side port 62 opens through a longitudinal sidewall of depending arm 54 in order to provide additional oxygen flow through nozzle 58. Most preferably main end port 60 has a diameter of 0.022 millimeters, while side port 62 has a diameter of 0.032 millimeters. With nozzle ports of the preferred sizes, when oxygen duct 18 is connected to an oxygen source of fifty pounds per square inch and side port 62 is closed, end port 60 will preferably provide a flow rate of ten liters per minute. With both end port 60 and side port 62 open and duct 18 connected to a fifty psi oxygen source, nozzle 58 will preferably provide a flow rate of forty liters per minute. End port 60 therefore alone provides a normal or low flow rate condition, while the opening of side port 62 results in a high flow rate condition.

Capillary tube 20 (FIG. 1) includes an upper mounting bracket or tab 70 connected to the sidewall of nozzle 58. Mounting tab 70 provides a solid mount for capillary tube 20 which depends down through housing 14 to a lower end 72 beneath coupling 44. Lower end 72 extends down to a capillary tube opening (not shown) spaced sufficiently beneath coupling 44 so as to be located in the humidifying liquid contained in fluid reservoir 22. Projecting from the side of capillary tube 20 directly beneath nozzle 58 is an entrainment outlet 74. Entrainment outlet 74 is positioned at the oxygen jet emanating from end port 60 of nozzle 58, and most preferably has an inside diameter of 0.027 millimeters. The passage of the oxygen jet from nozzle 58 over entrainment outlet 74 induces a vacuum in capillary tube 20, thus causing liquid to be drawn up from fluid reservoir 22 to be fed through entrainment outlet 74 into the oxygen jet emanating from end port 60, thus becoming entrained in the oxygen in a fine mist.

On the side of housing 14 is an atmosphere inlet port 80. Inlet port 80 is situated so as to open into mixing chamber 56 laterally adjacent nozzle 58. Inlet port 80 is shown in a preferred form as a rectangular opening. Alternatively, inlet port 80 may be configured in other shapes and dimensions. Inlet port 80 is dimensioned and located so that the oxygen jet emanating from nozzle 58 induces atmospheric gases to enter into housing 14 through inlet port 80, rather than oxygen passing through duct 18 and escaping to the atmosphere out inlet port 80. In this regard, side port 62 is oriented so as to not direct oxygen flow directly out inlet port 80, but rather toward a closed sidewall of housing 14. Alternatively a pair of atmosphere ports 80 are located on opposite sides of housing 14. In this alternative embodiment the atmosphere port 80 on the opposite side of housing 14 is identical to the port 80 located on the front of housing 14, and therefore only one inlet port 80 is described.

Housing collar 16 is telescopically slidably received over cylindrical housing 14. Housing collar 16 is also generally cylindrical in shape having open ends through which housing 14 is received. Collar 16 is dimensioned to be snugly seated on housing 14 and form a tight seal therewith, but housing collar 16 is still sufficiently loose to both rotate and slide vertically along housing 14. Housing 14 and housing collar 16 are therefore made of self-lubricating materials. Alternatively housing 14 and housing collar 16 may be fitted with seals, bearings and the like (not shown) in order to permit the relative movement but provide a tight seal.

In a lower region of housing collar 16 are a low flow rate atmosphere aperture 82 and a high flow rate atmosphere aperture 84. Atmosphere apertures 82 and 84 are located so as to each alternatively or selectively align with inlet port 80 when collar 16 is received on housing 14. Atmosphere apertures 82 and 84 are vertically spaced on housing collar 16 so that low flow rate atmosphere aperture 82 is located above high flow rate atmosphere aperture 84. Sliding housing collar 16 vertically up and down on housing 14 therefore shifts the alignment with the horizontal plane of inlet port 80 between upper low flow rate atmosphere aperture 82 and lower high flow rate atmosphere aperture 84, while duct collar 24 is simultaneously slid along nozzle 58 to regulate the opening of side port 62. Additionally, atmosphere apertures 82 and 84 are circumferentially offset from each other along the circumference of housing collar 16. Atmosphere apertures 82 and 84 are therefore not vertically aligned, although there may be some overlap when apertures 82 and 84 are considered along a vertical line on housing collar 16. This vertical nonalignment is used in the simultaneous adjustment of oxygen flow rate and atmospheric gas introduction as described below.

Atmosphere apertures 82 and 84 are each configured to overlay and slidably restrict atmosphere inlet port 80 as housing collar 16 is rotated about housing 14. Housing collar 16 operates in conjunction with atmosphere inlet port 80 to function as an atmosphere inlet valve to mixing chamber 56. For either of atmosphere apertures 82 and 84, the degree of alignment between the atmosphere aperture and atmosphere inlet port 80 determines the amount of atmospheric gases that are drawn into mixing chamber 56 as a result of the air jet through nozzle 58.

Alternatively, in an embodiment having inlet ports 80 located on opposite sides of housing 14, another set of atmosphere apertures 82 and 84 are located on the opposite side of collar 16 so as to selectively align with that inlet port 80. Additional sets of inlet ports 80 and atmosphere apertures 82 and 84 may be provided.

Located above atmosphere aperture 82 on housing collar 16 is a track slot 86. Track slot 86 receives lateral arm 53 of duct 18, so that lateral arm 53 operates as a track follower or guide in track slot 86. Track 86 and duct 18 cooperate to direct the adjustment of housing collar 16 on housing 14, both in the vertical sliding of housing collar 16 as well as the rotation of collar 16 on housing 14. Track slot 86 has an upper generally horizontal course 88, a middle generally vertical course 90 and a lower generally horizontal course 92. Track slot 86 therefore has an overall "Z" configuration. Track slot 86 permits housing collar 16 to rotate when lateral arm 53 is seated in either upper course 88 or lower course 92. Housing collar 16 is permitted to be slid vertically when lateral arm 53 is seated in middle course 90.

Track slot 86 and atmosphere apertures 82, 84 are cooperatively spaced such that when lateral arm 53 is seated in upper course 88 (see FIG. 2), low flow rate atmosphere aperture 82 is aligned with the horizontal plane of atmosphere inlet port 80 and when lateral arm 53 is seated in lower course 92 (see FIG. 3), high flow rate atmosphere aperture 84 is aligned with the horizontal plane of atmosphere inlet port 80. With lateral arm 53 seated in upper course 88, housing collar 16 may be rotated so as to vary the alignment between low flow rate atmosphere aperture 82 and inlet port 80, thus adjusting the restriction of inlet port 80, and adjusting the fraction of inspired oxygen between 0.28 and 0.5. When lateral arm 53 is seated in lower course 92 housing collar 16 may be rotated so as to vary the alignment between high flow rate atmosphere aperture 84 and inlet port 80, also adjusting the restriction of inlet port 80, and adjusting the fraction of inspired oxygen between 0.5 and 1.0. As lateral arm 53 is slid along vertical middle course 90, alignment with inlet port 80 is shifted between atmosphere aperture 82 and atmosphere aperture 84. Along a horizontal edge of atmosphere apertures 82 and 84 are indicia 94 representing the calibrated value of fraction of inspired oxygen that will pass through nebulizer device 12 when a sidewall of inlet port 80 is aligned with that particular indicia 94.

Alternatively track slot 86 may have alternative configurations. For example, the three track courses 88, 90 and 92 may each be sloped so as to each produce some degree of vertical movement and rotation of housing collar 16. In such an embodiment atmosphere apertures 82 and 84 are cooperatively spaced accordingly. Atmosphere apertures 82 and 84 may alternatively be a single configured aperture, such as for example, the section of housing collar 16 spacing apertures 82 and 84 may be removed to form a single "Z" shaped aperture.

Duct collar 24 is coupled to housing collar 16 through a mounting bar 100 (FIG. 1). Mounting bar 100 extends along a diameter of collar 16 and is received through a pair of adjustment slots 102 in upper end 40 of collar 16. Adjustment slots 102 permit mounting bar 100 to remain stationary as housing collar 16 is rotated, yet cause mounting bar 100 to be raised and lowered as housing collar 16 is shifted vertically. A pair of enlarged end lugs 104 prevent the ends of mounting bar 100 from pulling back through adjustment slots 102. A connecting bracket 106 (FIG. 6) depends from the midpoint of mounting bar 100 down to duct collar 24. As housing collar 16 is raised and lowered duct collar 24 is thereby raised and lowered. As shown in FIGS. 4-6, duct collar 24 is a cylindrical split ring that is snugly received over nozzle 58. Duct collar 24 is spaced beneath mounting bar 100 such that when lateral arm 53 is seated in upper course 88, duct collar 24 closes off side port 62 as shown in FIG. 4. When lateral arm 53 is seated in lower course 92, duct collar 24 is slid above side port 62, thereby opening side port 62 as shown in FIG. 5.

Figure 2:
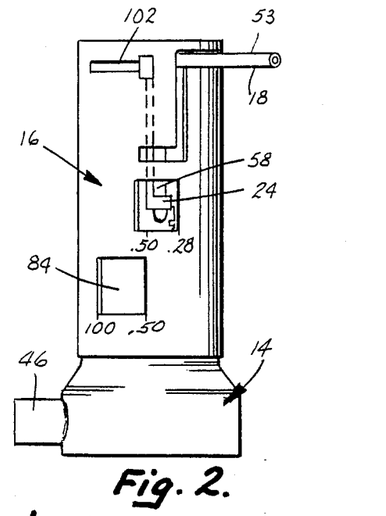
FIG. 2 is a front elevational view of the nebulizer device of FIG. 1, shown in a reduced flow rate, 0.28 fraction of inspired oxygen condition.
Figure 3:
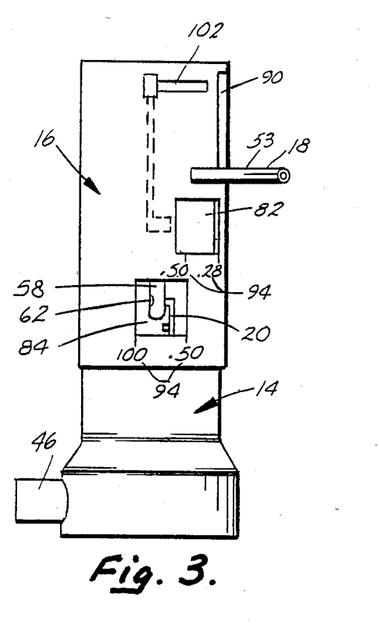
FIG. 3 is a front elevational view of the nebulizer device of FIG. 1, shown in an increased flow rate, 0.5 fraction of inspired oxygen condition.
Figure 7:
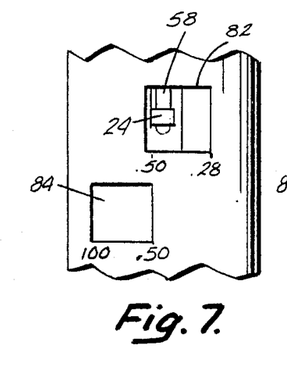
FIGS. 7, 8 and 9 are fragmentary, front elevational views of the nebulizer device of FIG. 1, showing three settings or adjustments of fraction of inspired oxygen provided thereby.
Figure 8:
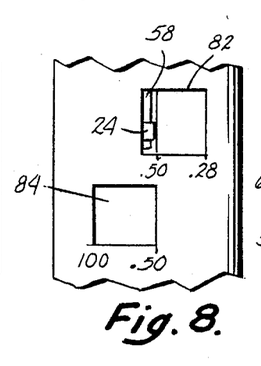

In operation, with oxygen duct 18 coupled to a fifty psi oxygen source, lateral arm 53 seated in upper course 88 and collar 16 rotated to a position shown in FIG. 2, duct collar 24 closes side port 62. Low flow rate atmosphere aperture 82 aligns with inlet port 80. The configurations and dimensions of atmosphere inlet port 80 and atmosphere aperture 82 are such that in this fully open but low flow rate condition, a 0.28 fraction of inspired oxygen or twenty eight percent oxygen mixture is supplied to the patient. This calibration takes into account the fact that atmospheric gases typically include 0.21 fraction of inspired oxygen, or twenty one percent oxygen. As housing collar 16 is rotated to a condition shown in FIG. 7, the alignment between inlet port 80 and atmosphere aperture 82 is adjusted so as to partially restrict inlet port 80. The amount of atmospheric gases entrained are thus reduced, causing the oxygen passing through oxygen duct 18 to make up a higher percentage of the overall gas mixture supplied to the patient. As housing collar 16 is further rotated to a condition shown in FIG. 8, the misalignment of inlet port 80 and atmosphere aperture 82 further restricts inlet port 80. Some flow is permitted in through atmosphere inlet port 80, which, when mixed with the oxygen flow of ten liters per minute through end port 60, results in a 0.5 fraction of inspired oxygen.

Figure 9:
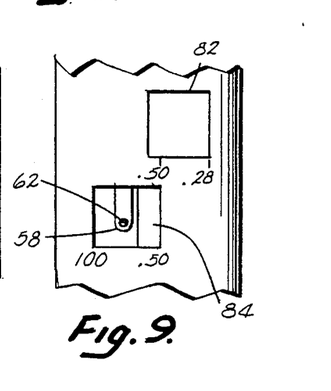

In order to achieve an increased fraction of inspired oxygen but still retain a high flow rate to the patient, housing collar 16 is slid vertically with lateral arm 53 passing along middle course 90. Collar 16 is thus shifted to a condition shown in FIG. 3. In this condition duct collar 24 is slid above side port 62 as in FIG. 5, resulting in a forty liter per minute flow of oxygen through nozzle 58. High flow rate atmosphere aperture 84 is fully aligned with inlet port 80 to provide an increased flow of atmospheric gases through inlet port 80. This increased flow of atmospheric gas compensates for the increased flow of oxygen through nozzle 58, so that high flow rate atmosphere aperture 84 is also calibrated for a 0.5 fraction of inspired oxygen. Rotation of housing collar 16 to a condition shown in FIG. 9 causes misalignment of inlet port 80 and atmosphere aperture 84, thus restricting flow through inlet port 80. Again, atmosphere aperture 84 is calibrated to provide the indicated flow at the higher flow rate through nozzle 58. Additional indicia 94 for additional calibrated settings may be provided. When housing collar 16 is fully rotated inlet port 80 and atmosphere aperture 84 are wholly misaligned and inlet port 80 is closed off (not shown). In this closed condition only oxygen flowing through oxygen duct 18 is supplied to the patient, although a rate of forty liters per minute is still maintained.

Atmosphere entraining valve 26 (FIG. 10) is coupled to a standard respiratory tubing 110 preferably having an inside diameter of twenty two millimeters and which leads from nebulizer tubing outlet 46. On the downstream end of entraining valve 26 is a wider diameter respiratory tubing 112. Preferably wider diameter respiratory tubing 112 has an inside diameter of approximately thirty millimeters and leads into a respiration mask 114. Respiration mask 114 provides a means for connecting nebulizer device 12 to the patient, although alternatively other mechanisms may be used such as oxygen tents, tracheotomy pieces or the like.

As shown in FIG. 11, entraining valve 26 includes a narrow cylindrical tube that forms a nozzle 120. Most preferably nozzle 120 has an inside diameter of approximately nine sixteenths of an inch. Nozzle 120 projects into a rigid cylindrical valve body 122. A generally rectangular aperture forms an atmosphere inlet port 124 on either side of valve body 122, most preferably each inlet port 124 being approximately one and a quarter inch by one and an eighth inch. Alternatively other configurations and dimensions may be provided for atmosphere inlet ports 124. Nozzle 120 projects into the central mixing chamber region of valve body 122 and ends in a nozzle outlet 126. Preferably nozzle 120 projects approximately three quarters of an inch into valve body 122 and approximately three eighths inch past the downstream edges of atmosphere inlet ports 124. A valve collar 128 is slidably received over valve body 122 so as to snugly friction grip valve body 122. Valve collar 128 has a length sufficient to completely cover and block atmospheric inlet ports 124 when collar 128 is slid into registry or alignment with outlets 126. Marked along a longitudinal side of atmosphere inlet ports 124 are calibration indicia 130. Most preferably additional atmosphere entraining valve 26 and wider diameter respiratory tubing 112 are approximately nine inches in length overall.

Narrowed nozzle outlet 126 is located laterally adjacent inlet ports 124 so as to provide a venturi-like jet that is directed toward wider diameter respiratory tubing 112 and which induces atmospheric gases to be drawn in through inlet ports 124. Atmosphere inlet ports 124 are configured and dimensioned so as to result in an output of 0.24 fraction of inspired oxygen when a gas mixture having a 0.28 fraction of inspired oxygen is supplied to entraining valve 26 and valve collar 128 is in a fully opened condition. Collar 128 may be slid along valve body 122 and aligned with calibrated indicia 130 so as to selectively adjust the restriction of atmosphere inlet ports 124 and thus adjust the resulting fraction of inspired oxygen supplied to the patient. As will be recognized, when valve collar 128 is slid to a fully closed condition, the fraction of inspired oxygen does not change as the gas mixture moves through entraining valve 26.

As shown in FIG. 10, the humidified gas is supplied directly into respiratory mask 114. Respiratory mask 114 has a pair of side vents 132. Side vents 132 permit the introduction of additional atmospheric gas in the event that the patient's breathing requires a flow rate higher than that provided by nebulizer device 12, as well as provide exhalation ports for the patient. Shown in FIG. 11 is an alternative patient connecting system that includes an alternative "T" connector 134. Connector 134 is preferably used with a tracheotomy piece or the like and therefore provides an additional vent. Connector 134 includes a patient connecting branch 136. Branch 136 preferably has a fifteen millimeter inner diameter so as to couple with standard endotracheal tube or tracheostomy tube adapters or the like. A vent branch 138 vents to atmosphere and permits the patient to draw in additional atmospheric gases in the event that the flow rate of nebulizer device 12 is insufficient.

A deflecting shield or tube (not shown) may alternatively be located in nebulizer housing 14 in order to collect excessive fluid and reduce fluid collection along tubing outlet 46 and the like. The deflecting shield preferably consists of an open ended cylindrical tube concentrically mounted within housing 14 but spaced from the inner wall of housing 14 so as to surround the oxygen jet region beneath nozzle 58. Atmospheric gas flows in through aperture 84 and around the open ends of the shield to the nozzle region. As the fluid is entrained in the oxygen, excessive mist strikes and collects on the shield, thereafter running down the shield and falling into fluid reservoir 22.

It is to be understood that the above is a description of the preferred embodiment and that one skilled in the art will recognize that various modifications or improvements may be made without departing from the spirit of the invention disclosed herein. The scope of protection afforded to be determined by the claims which follow and the breadth of interpretation that the law allows.

The embodiments of the invention in which an exclusive property or privilege is claimed are as follows.

1. A nebulizer device for use with a source of sxygen flow, a source of atmospheric gas, a fluid supply vessel and respiratory ducting equipment leading to a patient, comprising:

a housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient;

means for selectively adjusting the restriction of said oxygen inlet;

means for supplying liquid from said fluid supply vessel to said mixing chamber proximate said oxygen inlet duct;

said mixing chamber having an atmosphere inlet port communicating with said atmospheric gas source;

means for selectively restricting said atmosphere inlet port to regulate the rate of gas flow therethrough, said atmosphere inlet port restricting means including an atmosphere restricting panel movably mounted on said housing so as to selectively block said atmosphere inlet port;

said atmosphere inlet port restricting means coupled to said oxygen inlet duct restriction adjusting means such that adjusting the restriction of said oxygen inlet duct simultaneously adjusts said atmosphere inlet port restricting means;

said oxygen inlet duct restriction adjusting means including said oxygen inlet duct having a plurality of oxygen outlet ports disposed in said mixing chamber and means for selectively blocking at least one of said oxygen outlet ports while simultaneously adjusting said atmosphere inlet port restricting means, said oxygen outlet port blocking means including an oxygen blocking panel movably mounted on said housing to selectively block said one oxygen outlet port, said oxygen blocking panel coupled to said atmosphere restricting panel, whereby the oxygen flow through the nebulizer can be increased and decreased while the atmospheric gas flow is simultaneously adjusted to provide a selected gas mixture to said patient.

2. The nebulizer device of claim 1, wherein:

said oxygen blocking panel is configured to adjust the blocking of said one oxygen outlet port when moved in a first direction but maintain the blocking of said oxygen outlet port when moved in a second direction nonparallel to said first direction;

said atmosphere restricting panel configured to adjust the blocking of said atmosphere inlet port when moved in said first direction and when moved in said second direction.

3. The nebulizer device of claim 2, wherein:

said atmosphere restricting panel includes an atmosphere collar movably mounted on said housing so as to move in said first direction and said second direction, said atmosphere collar coupled to said oxygen blocking panel;

said atmosphere collar having at least one atmosphere aperture therethrough, said atmosphere aperture configured to selectively align with said atmospheric inlet port and adjustably restrict said atmosphere inlet port as said atmosphere collar is moved in said first direction and in said second direction.

4. The nebulizer device of claim 3, wherein:

said oxygen blocking panel includes a duct collar movably mounted on said oxygen inlet duct.

5. The nebulizer device of claim 4, wherein:

said oxygen inlet duct has a longitudinal side and a mixing chamber end;

said one oxygen outlet port opens through said longitudinal side and another of said oxygen outlet ports opens through said mixing chamber end.

6. A nebulizer device for use with a source of oxygen flow, a source of atmospheric gas, a fluid supply vessel and respiratory ducting equipment leading to a patient, comprising:

a housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient, said oxygen inlet duct having a longitudinal side and mixing chamber end, and said oxygen inlet duct having a plurality of oxygen outlet ports disposed in said mixing chamber, at least one oxygen outlet port opening through said longitudinal side and another of said oxygen outlet ports opening through said mixing chamber end;

means for supplying liquid from said fluid supply vessel to said mixing chamber proximate said oxygen inlet duct;

said mixing chamber having an atmosphere inlet port communicating with said atmospheric gas source;

means for selectively restricting said atmosphere inlet port to regulate the rate of gas flow therethrough, said atmosphere inlet port restricting means including an atmosphere restricting panel movably mounted on said housing so as to selectively block said atmosphere inlet port, said atmosphere restricting panel including an atmosphere collar movably mounted on said housing and configured to adjust the blocking of said atmosphere inlet port when moved in a first direction and when moved in a second direction nonparallel to said first direction;

said atmosphere collar having at least one atmosphere aperture therethrough, said atmosphere aperture configured to selectively align with said atmospheric inlet port and adjustably restrict said atmosphere inlet port as said atmosphere collar is moved in said first direction and in said second direction;

means for selectively adjusting the restriction of said oxygen inlet duct and simultaneously adjusting said atmosphere inlet port restricting means, said oxygen inlet duct restriction adjusting means including means for selectively blocking said one of said oxygen outlet ports while simultaneously adjusting said atmosphere inlet port restricting means, said oxygen outlet port blocking means including an oxygen blocking panel movably mounted on said housing to selectively block said one oxygen outlet port and said oxygen blocking panel coupled to said atmosphere collar;

said oxygen blocking panel configured to adjust the blocking of said one oxygen outlet port when moved in said first direction but maintain the blocking of said oxygen outlet port when moved in said second direction, said oxygen blocking panel including a duct collar movably mounted on said oxygen inlet duct;

one of said housing and said atmosphere collar having a guide track with track courses and the other of said housing and said atmosphere collar having a track follower registering with said track, said track having a first track course extending in said first direction and joining two second track courses, said second track courses extending in said second direction, whereby the oxygen flow through the nebulizer can be increased and decreased while the atmospheric gas flow is simultaneously adjusted to provide a selected gas mixture to said patient.

7. The nebulizer device of claim 6, further comprising:

respiratory ducting coupled to said housing so as to be disposed downstream of said oxygen outlet ports and having means for securing to a person using said nebulizer;

a ducting valve disposed on said respiratory ducting, said ducting valve selectively venting atmospheric gases into said respiratory ducting.

8. A nebulizer device for use with a source of oxygen flow, a source of atmospheric gas, a fluid supply vessel and respiratory ducting equipment leading to a patient, comprising:

housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient;

means for selectively adjusting the restriction of said oxygen inlet;

means for supplying liquid from said fluid supply vessel to said mixing chamber proximate said oxygen inlet duct;

said mixing chamber having an atmosphere inlet port communication with said atmospheric gas source;

means for selectively restricting said atmosphere inlet port to regulate the rate of gas flow therethrough, said atmosphere inlet port restricting means including an atmosphere restricting panel movably mounted on said housing so as to selectively block said atmosphere inlet port;

said atmosphere inlet port restricting means coupled to said oxygen inlet duct restriction adjusting means such that adjusting the restriction of said oxygen inlet duct simultaneously adjusts said atmosphere inlet port restricting means, said oxygen inlet duct restriction adjusting means including said oxygen inlet duct having a plurality of oxygen outlet ports disposed in said mixing chamber and means for selectively blocking at least one of said oxygen outlet ports while simultaneously adjusting said atmosphere inlet port restricting means;

said oxygen outlet port blocking means including an oxygen blocking panel movably mounted on said housing to selectively block said one oxygen outlet port, said oxygen blocking panel coupled to said atmosphere restricting panel, said oxygen blocking panel configured to adjust the blocking of said one oxygen outlet port when moved in a first direction but maintain the blocking of said oxygen outlet port when moved in a second direction nonparallel to said first direction;

said atmosphere restricting panel configured to adjust the blocking of said atmosphere inlet port when moved in said first direction and when moved in said direction, said atmosphere restricting panel including a housing collar movably mounted on said housing so as to move in said first direction and said second direction, said housing collar coupled to said oxygen blocking panel;

said housing collar having at least two atmosphere apertures therethrough, said atmosphere apertures each configured to separately selectively align with said atmosphere inlet port and adjustably restrict said atmosphere inlet port as said housing collar is moved in said second direction, said atmosphere apertures located to shift alignment with said atmosphere inlet port between said atmosphere apertures as said housing collar is moved in said first direction, whereby the oxygen flow through the nebulizer can be increased and decreased while the atmospheric gas flow is simultaneously adjusted to provide a selected gas mixture to said patient.

9. The nebulizer device of claim 8, wherein:

said oxygen blocking panel includes a duct collar movably mounted on said oxygen inlet duct.

10. The nebulizer device of claim 9, wherein:

said oxygen inlet duct has a longitudinal side and a mixing chamber end;

said one oxygen outlet port opens through said longitudinal side and another of said oxygen outlet ports opens through said mixing chamber end.

11. The nebulizer device of claim 10, wherein:

one of said housing and said housing collar has a guide track with track courses and the other of said housing and said housing collar has a follower registering with said guide track, said track having a first track course extending in said first direction and joining two second track courses, said second track courses extending in said second direction.

12. A nebulizer device for use with a source of oxygen flow, a source of atmospheric gas, a fluid supply vessel and respiratory ducting equipment leading to a patient, comprising:

a housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient;

means for selectively adjusting the restriction of said oxygen inlet;

means for supplying liquid from said fluid supply vessel to said mixing chamber proximate said oxygen inlet duct;

said mixing chamber having an atmosphere inlet port communicating with said atmospheric gas source;

means for selectively restricting said atmosphere inlet port to regulate the rate of gas flow therethrough, said atmosphere inlet port restricting means includes an atmosphere restricting panel movably mounted on said housing so as to selectively block said atmosphere inlet port;

said atmosphere inlet port restricting means coupled to said oxygen inlet duct restriction adjusting means such that adjusting the restriction of said oxygen inlet duct simultaneously adjusts said atmosphere inlet port restricting means, said atmosphere restricting panel coupled to said oxygen inlet duct restriction adjusting means so as to adjust the restriction of said oxygen inlet duct as said atmosphere restricting panel is moved in a first direction;

said atmosphere restricting panel having at least one atmosphere aperture therethrough, said atmosphere aperture configured to selectively align with said atmosphere inlet port and adjustably restrict said atmosphere inlet port as said atmosphere restricting panel is moved in a second direction nonparallel to said first direction, whereby the oxygen flow through the nebulizer can be increased and decreased while the atmospheric gas flow is simultaneously adjusted to provide a selected gas mixture to said patient.

13. A nebulizer device for use with a source of oxygen flow, a source of atmospheric gas, a fluid supply vessel and respiratory ducting equipment leading to a patient, comprising:

a housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient;

means for selectively adjusting the restriction of said oxygen inlet;

means for supplying liquid from said fluid supply vessel to said mixing chamber proximate said oxygen inlet duct;

said mixing chamber having an atmosphere inlet port communicating with said atmospheric gas source;

means for selectively restricting said atmosphere inlet port to regulate the rate of gas flow therethrough;

said atmosphere inlet port restricting means coupled to said oxygen inlet duct restriction adjusting means such that adjusting the restriction of said oxygen inlet duct simultaneously adjusts said atmosphere inlet port restricting means;

said atmosphere inlet port restricting means including an atmosphere restricting panel movably mounted on said housing so as to selectively block said atmosphere inlet port, said atmosphere restricting panel coupled to said oxygen inlet duct restriction adjusting means so as to adjust the restriction of said oxygen inlet duct as said atmosphere restricting panel is moved in a first direction;

said atmosphere restricting panel having at least two atmosphere apertures therethrough, said atmosphere apertures each configured to separately, selectively align with said atmosphere inlet port and adjustably restrict said atmosphere inlet port as said atmosphere restricting panel is moved in a second direction nonparallel to said first direction, said atmosphere apertures located to shift alignment with said atmosphere inlet port between said atmosphere apertures as said atmosphere restricting panel is moved in said first direction, whereby the oxygen flow through the nebulizer can be increased and decreased while the atmospheric gas flow is simultaneously adjusted to provide a selected gas mixture to said patient.

14. The nebulizer device of claim 13, wherein:

said atmosphere restricting panel includes a housing collar movably mounted on said housing.

15. A nebulizer device for use with a source of oxygen flow, a source of atmospheric gas, a fluid supply vessel and respiratory ducting equipment leading to a patient, comprising:

a housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient;

means for selectively adjusting the restriction of said oxygen inlet;

means for supplying liquid from said fluid supply vessel to said mixing chamber proximate said oxygen inlet duct;

said mixing chamber having an atmosphere inlet port communicating with said atmospheric gas source;

means for selectively restricting said atmosphere inlet port to regulate the rate of gas flow therethrough;

said atmosphere inlet port restricting means coupled to said oxygen inlet duct restriction adjusting means such that adjusting the restriction of said oxygen inlet duct simultaneously adjusts said atmosphere inlet port restricting means;

said atmosphere inlet port selective restricting means including a housing collar movably mounted on said housing so as to move in a first direction and in a second direction nonparallel to said first direction, said housing collar coupled to said oxygen inlet duct restriction adjusting means so as to adjust the restriction of said oxygen inlet duct as said housing collar is moved in said first direction;

said housing collar having at least two atmosphere apertures therethrough, said atmosphere apertures each configured to separately, selectively align with said atmosphere inlet port and adjustably restrict said atmosphere inlet port as said housing collar is moved in said second direction, said atmosphere apertures located to shift alignment with said atmosphere inlet port between said atmosphere apertures as said housing collar is moved in said first direction, whereby the oxygen flow through the nebulizer can be increased and decreased while the atmospheric gas flow is simultaneously adjusted to provide a selected gas mixture to said patient.

16. The nebulizer device of claim 15, further comprising:

respiratory ducting coupled to said housing so as to be disposed downstream of said oxygen inlet duct and having means for securing to a person using said nebulizer;

a ducting valve disposed on said respiratory ducting, said ducting valve selectively venting atmospheric gases into said respiratory ducting.

17. The nebulizer device of claim 16, wherein:

said ducting valve is disposed at a valving region of said respiratory ducting, said valving region having a first inner cross-sectional area;

said respiratory ducting having an upstream outlet opening into said valving region, said upstream outlet having a second inner cross-section area less than said first cross-sectional area.

18. The nebulizer device of claim 17, wherein:

said upstream outlet includes a nozzle projecting into said valving region.

19. The nebulizer device of claim 18, wherein:

said ducting valve includes a ducting opening on said respiratory ducting at said valving region and a valve collar movably mounted on said respiratory ducting so as to selectively restrict said ducting opening.

20. The nebulizer device of claim 19, wherein:

said ducting valve has a configuration and dimensions when in an opened condition to lower the oxygen content of a gas mixture having 28 percent oxygen to 24 percent oxygen.

21. The nebulizer device of claim 16, wherein:

said ducting valve has a configuration and dimensions when in an opened condition to lower the oxygen content of a gas mixture having 28 percent oxygen to 24 percent oxygen.

22. The nebulizer device of claim 15, wherein:

said nebulizer is adapted to provide a gas flow through said nebulizer;

said means for selectively adjusting the restriction of said oxygen inlet duct and said means for selectively restricting said atmosphere inlet port selectively adjust the percentage of oxygen in said gas flow through said nebulizer through a range from 28 percent to 100 percent 23. A nebulizer device for use with a source of oxygen flow, a source of atmospheric gas, a fluid supply container and respiratory ducting equipment leading to a patient, comprising:

a housing having means for coupling to said fluid supply container, a mixing chamber therein and an atmosphere inlet port opening into said mixing chamber;

an oxygen duct having means for coupling to said source of oxygen flow, said oxygen duct having an oxygen outlet disposed in said mixing chamber;

means for conveying fluid from said fluid supply container to said mixing chamber proximate said oxygen outlet;

an atmosphere restricting gate movably mounted on said housing so as to move in a first direction and a second direction nonparallel to said first direction, said atmosphere restricting gate configured to adjustably close said atmosphere inlet port and thereby selectively restrict air flow therethrough as said atmosphere restricting gate is moved in said first direction an in said second direction;

an oxygen restricting gate movably mounted on said oxygen duct so as to move in at least said first direction, said oxygen restricting gate coupled to said atmosphere restricting gate and configured to adjustably close said oxygen outlet and thereby selectively restrict oxygen flow therethrough as said atmosphere restricting gate is moved in said first direction, and said oxygen restricting gate coupled to said atmosphere restricting gate so as to not vary restriction of oxygen flow through said oxygen outlet as said atmosphere restricting gate is moved in said second direction.

24. The nebulizer device of claim 23, wherein:

said oxygen duct has a longitudinal side, said oxygen outlet has a first oxygen port on said longitudinal side;

said oxygen restricting gate includes an oxygen collar longitudinally slidable along said oxygen duct.

25. The nebulizer device of claim 23, wherein:

said atmosphere restricting gate includes a housing collar slidably and rotatably mounted on said housing, said housing collar having at least one atmosphere vent therethrough that is selectively alignable with said atmosphere inlet port.

26. The nebulizer device of claim 25, wherein:

said housing collar has at least two atmosphere vents therethrough.

27. The nebulizer device of claim 25, wherein:

said oxygen duct has a longitudinal side, said oxygen outlet has a first oxygen port on said longitudinal side;

said oxygen restricting gate includes an oxygen collar longitudinally slidable along said oxygen duct.

28. The nebulizer device of claim 27, wherein:

said oxygen duct has a nozzle end, and said oxygen duct has a second oxygen port on said nozzle end.

29. The nebulizer device of claim 23, further comprising:

respiratory tubing coupled to said housing;

an atmosphere entraining valve disposed on said respiration tubing, said atmosphere entraining valve selectively inletting atmospheric gases into said respiratory tubing.

30. The nebulizer device of claim 29, wherein:

said atmosphere entraining valve has a valve body with a valve aperture thereon;

a valve collar slidably mounted on said valve body to selectively close said valve aperture.

31. The nebulizer device of claim 29, wherein:

said valve body has a valve cross-sectional area;

a nozzle coupled to said respiratory tubing and projecting into said valve body proximate said valve aperture, said nozzle having a nozzle cross-sectional area less than said valve cross-sectional area.

32. A nebulizer device for use with a source of oxygen flow, a source of atmospheric gas, a fluid supply vessel and respiratory ducting equipment leading to a patient, comprising:

a housing having means for coupling said housing to said fluid supply vessel, said housing having a mixing chamber therein;

an oxygen inlet duct coupled to said housing and adapted for connection to said source of oxygen flow, said oxygen inlet duct opening into said mixing chamber to direct oxygen flow toward the patient, said oxygen inlet duct having a longitudinal side with a first oxygen outlet port opening therethrough, and said oxygen inlet duct having a mixing chamber end with a second oxygen outlet port opening therethrough;

means for supplying liquid from said fluid supply vessel to said mixing chamber proximate at least said second oxygen inlet duct;

said mixing chamber having an atmospheric inlet port communicating with said atmospheric gas source;

means for selectively restricting said atmosphere inlet port to regulate the rate of gas flow therethrough, said atmosphere inlet port restricting means including a housing collar movably mounted on said housing so as to move in a first direction and in a second direction nonparallel to said first direction, said housing collar including at least two atmosphere apertures therethrough, said atmosphere apertures each configured to separately selectively align with said atmosphere inlet port and adjustably restrict said atmosphere inlet port as said housing collar is moved in said second direction, said atmosphere apertures located to shift alignment with said atmosphere inlet port between said atmosphere apertures as said housing collar is moved in said first direction;

means for selectively adjusting the restriction of said oxygen inlet duct and simultaneously adjusting said atmosphere inlet port restricting means, said oxygen inlet duct restriction adjusting means including a duct collar movably mounted on said oxygen inlet duct so as to selectively block said first oxygen outlet port, said duct collar configured to adjust the blocking of said first oxygen outlet port when moved in said first direction but maintained the blocking of said first oxygen outlet port when moved in said second direction, and said duct collar coupled to said housing collar;

one of said housing and said housing collar having a guide track with track courses and the other of said housing and said housing collar having a follower registering with said guide track, said track having a first track course extending in said first direction and joining two second track courses, said second track courses extending in said second direction, whereby the oxygen flow through the nebulizer can be increased and decreased while the atmospheric gas flow is simultaneously adjusted to provide a selected gas mixture to said patient.

33. The nebulizer device of claim 32, further comprising:

respiratory ducting coupled to said housing so as to be disposed downstream of said oxygen outlet port and having means for securing to a person using said nebulizer;

a ducting valve disposed on said respiratory ducting, said ducting valve selectively venting atmospheric gases into said respiratory ducting.

* * * * *

UNITED STATES PATENT AND TRADEMARK OFFICE
CERTIFICATE OF CORRECTION

PATENT NO. : 4,886,055

DATED : December 12, 1989

INVENTOR(S) : John M. Hoppough

It is certified that error appears in the above-identified patent and that said Letters Patent is hereby corrected as shown below:

Column 9, Claim 1, Line 20;
  "sxygen" should be --oxygen--.

Column 11, Claim 8, Line 45;
  Before "housing" insert --a--. (1st occurrence)

Column 15, Claim 17, Line 14;
  "cross-section" should be --cross-sectional--.

Signed and Sealed this

Twentieth Day of August, 1991

Attest:

HARRY F. MANBECK, JR.

Attesting Officer

Commissioner of Patents and Trademarks